(12) United States Patent
Shahrokni et al.

(10) Patent No.: US 8,216,263 B2
(45) Date of Patent: *Jul. 10, 2012

(54) LANCET REMOVAL TOOL

(75) Inventors: Farzad M. Shahrokni, Eastleaze (GB);
Andrew Huckstep, Wantage (GB);
Oliver Paul Jones, Grove (GB); Paul Sen Yang, Witney (GB)

(73) Assignee: Abbott Diabetes Care Inc., Alameda, CA (US)

( * ) Notice: Subject to any disclaimer, the term of this patent is extended or adjusted under 35 U.S.C. 154(b) by 318 days.

This patent is subject to a terminal disclaimer.

(21) Appl. No.: 12/547,277

(22) Filed: Aug. 25, 2009

(65) Prior Publication Data

US 2010/0049231 A1 Feb. 25, 2010

Related U.S. Application Data

(63) Continuation of application No. 10/513,122, filed as application No. PCT/GB03/01207 on Mar. 24, 2003, now Pat. No. 7,597,700.

(30) Foreign Application Priority Data

Apr. 30, 2002 (GB) .................................. 0209868.9

(51) Int. Cl.
*A61B 17/32* (2006.01)
(52) U.S. Cl. ...................................................... 606/182
(58) Field of Classification Search .................. 606/181, 606/182; 600/583
See application file for complete search history.

(56) References Cited

U.S. PATENT DOCUMENTS

| | | | |
|---|---|---|---|
| 2,857,912 A | 10/1958 | Feinstone et al. | |
| 4,580,566 A | 4/1986 | Hsu | |
| 5,147,101 A | 9/1992 | Tiller | |
| 5,207,699 A | 5/1993 | Coe | |
| 5,385,571 A | 1/1995 | Morita | |
| 5,916,230 A | 6/1999 | Brenneman et al. | |
| 5,971,941 A * | 10/1999 | Simons et al. | 606/181 |
| 6,053,173 A | 4/2000 | Cary, III | |
| 7,597,700 B2 * | 10/2009 | Shahrokni et al. | 606/181 |

FOREIGN PATENT DOCUMENTS

FR 2797579 A1 * 2/2001

* cited by examiner

*Primary Examiner* — Gary Jackson
*Assistant Examiner* — Eric Blatt
(74) *Attorney, Agent, or Firm* — Edward J. Baba; Benjamin C. Pelletier; Bozicevic, Field & Francis LLP

(57) ABSTRACT

A lancet removal tool 26 comprises an elongate hollow body 28 having an opening 32 at one end. The opening 32 is bounded by resilient fingers 36 which can flex to expand the opening 32 to engage the body 16 of the lancet 14. Withdrawal of the tool 26 after engagement with the lancet body 16 causes the lancet 14 to be removed from the lancet device. Subsequently, the lancet 14 can be moved from the opening 32 into the interior of the tool 26. The tool 26 and the removal procedure enables lancets 14 to be removed without risk of injury or infection from contact with the contaminated needle 18 of the lancet 14.

10 Claims, 4 Drawing Sheets

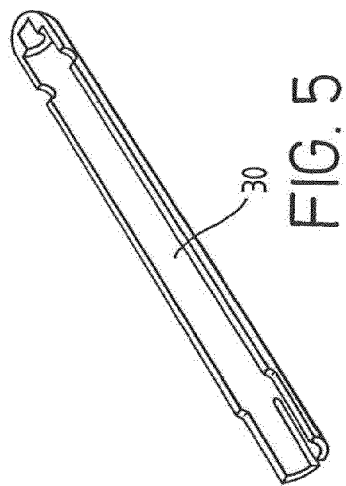
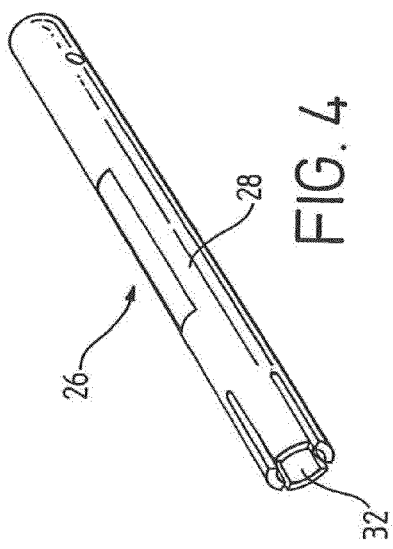
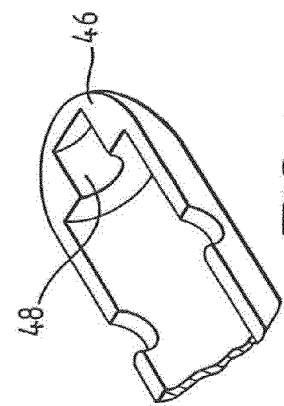
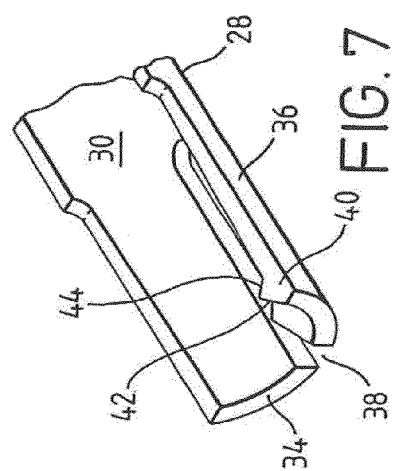
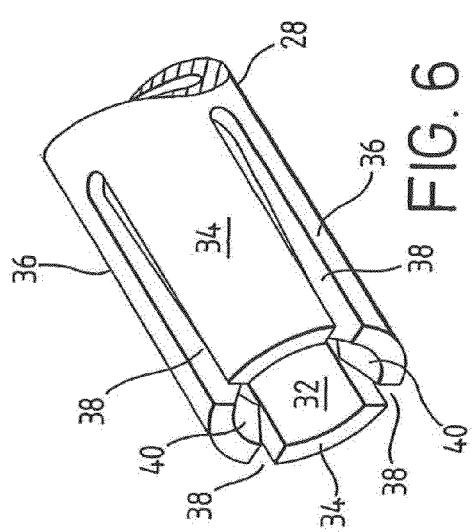

LANCET REMOVAL TOOL

This invention relates to a lancet removal tool for removing a lancet from a lancet device.

A lancet is commonly used to take a blood sample from a patient. Such lancets comprise a sharply pointed needle carried by a lancet body. The lancet may be used with a lancet device which includes a firing mechanism for driving the lancet forwards to prick the skin of a patient, and subsequently to withdraw the lancet. The lancet is removable from the lancet device because a fresh lancet is required for each blood sampling operation.

EP 1112717A discloses blood sampling apparatus including a lancet device. That apparatus is capable of performing a diagnostic test on the blood sample obtained in an automatic procedure.

After use, a lancet will be contaminated with the patient's blood. Consequently, the lancet must be removed from the lancet device and disposed of with great care, in order to avoid needlestick injuries to medical practitioners or other care workers performing the removal and disposal operation.

U.S. Pat. No. 5,797,942 discloses a lancet device which includes a removable end cap through which the pointed needle of the lancet momentarily extends to penetrate the skin of the patient during the lancing operation. The cap has a movable member which can be pushed inwards under finger pressure to engage the lancet frictionally, so that the removable cap can be withdrawn from the lancet device, taking the lancet with it. The cap can then be used to carry the lancet to a suitable disposal bin, where the movable member can be released to allow the lancet to drop into the bin.

With such a lancet device, the cap needs to be replaced on the lancet device before the next blood sampling operation can begin. However, the cap may become contaminated with blood from the lancet and consequently a false reading, or possibly even cross-infection, may occur in a subsequent blood sampling operation. Alternatively, the cap may be disposable with the lancet, but, while this may be acceptable in a relatively simple lancet device such as is shown in U.S. Pat. No. 5,797,942, disposal is less economic for more complex devices, such as the apparatus of EP 1112717A, in which the cap needs to support a vacuum, and plays a part in the operation of the diagnostic equipment.

Additionally, the end cap disclosed in U.S. Pat. No. 5,797,942 can accommodate only one lancet at a time with the result that, in practice, each lancet must be placed in the disposal bin, with or without the end cap, immediately after it is withdrawn from the lancet device. This is not always convenient. Furthermore, the frictional engagement of the lancet under positive finger pressure is not reliable, and there is the danger that if finger pressure is inadequate or is accidentally released, the lancet may be dropped.

According to the present invention there is provided a lancet removal tool for removing from a lancet device a lancet having a transverse body dimension of a predetermined size, the tool comprising a hollow body having an opening defined at least partially by a resilient element, whereby the opening is expandable against the resilient action of the resilient element from a rest condition, in which the transverse dimension of the opening is smaller than the predetermined size, to an expanded condition, in which the opening can receive the lancet body, with the lancet body then being retained within the opening under the resilient action of the resilient element.

In use of a lancet removal tool in accordance with the present invention, retention of the removed lancet does not require positive finger pressure by the user. This reduces the possibility of the lancet being accidentally dropped from the tool. Removal can thus be accomplished simply by pushing the lancet removal tool over the body of the lancet, the pointed needle of the lancet then being directed into the interior of the tool body. As the lancet removal tool is then pulled away from the lancet device, it carries the lancet with it. In a preferred embodiment, the interior of the body is large enough to receive the entire lancet, and preferably a plurality of lancets, so the lancet may be pushed completely through the opening into the interior of the body. If the body interior is sufficiently large, the tool can be used to withdraw several lancets before the body is full and needs either to be emptied of the lancets or disposed of together with the contained lancets.

The resilient element is preferably a resilient finger, and may be one of a plurality of fingers arranged around the opening. In a preferred embodiment, two oppositely disposed fingers are provided.

The fingers, or at least one of them, may have a ramp surface which assists in displacing the finger to expand the opening as the tool moves into contact with the lancet body. Where the tool has a pair of opposed fingers, the ramp surface may be provided on both of the fingers.

The or each finger having a ramp surface may also have a shoulder for engaging a rib or other formation on the lancet body. Thus, the ramp surface enables the respective finger to deflect as it passes over the rib, whereafter the finger snaps back under its resilient action to engage behind the rib. This provides positive engagement of the tool on the lancet to assist withdrawal of the lancet from the lancet device.

In a preferred embodiment, the body is elongate, and may have a cylindrical cross-section with an internal diameter just large enough to accept a lancet disposed lengthwise within the body. Thus, the body may be sufficiently long to accommodate a plurality of lancets disposed end-to-end within the body. In particular, it is desirable for the internal diameter of the tool body to be such that excessive tilting of the lancet body is prevented, so avoiding contact between the lancet needle and the internal wall of the tool body.

In such an embodiment, the resilient elements, for example in the form of fingers, may be integral with the body, formed by longitudinally extending slots at one end of the body.

The tool body may have a closed end so that removed lancets are trapped within the tool body. With this form of tool, the tool and the lancet or lancets within it must be disposed of together. Alternatively, the tool body may have a removable cap which normally closes an aperture through which lancets may be discharged, for example into a disposal bin, upon removal of the cap. The tool can then be reused. If the tool body is elongate, the expandable opening and the cap may be disposed at opposite ends of the body.

A second aspect of the present invention provides, in combination, at least one lancet and a lancet removal tool in accordance with the first aspect of the present invention, the lancet removal tool being sized for removal of the or each lancet from a lancet device. The lancet may have a rib for engagement by the resilient element of the tool.

According to a third aspect of the present invention, there is provide blood sampling equipment including a lancet, and a lancet removal tool in accordance with the first aspect of the present invention, for removing the lancet from a lancet device of the blood sampling equipment.

According to a fourth aspect of the present invention, there is provided a method of removing a lancet from a lancet device using a lancet removal tool in accordance with the first aspect of the invention.

For a better understanding of the present invention, and to show how it may be carried into effect, reference will now be made, by way of example, to the accompanying drawings, in which:

FIG. 4 shows the lancet removal tool;

FIG. 5 is a perspective longitudinal sectional view of the lancet removal tool;

FIG. 6 is an enlarged view of one end of the tool shown in FIG. 4;

FIG. 7 is an enlarged view of one end of the sectioned tool as shown in FIG. 5; and FIG. 8 shows the other end of the sectioned tool shown in FIG. 5.

Figure 1:
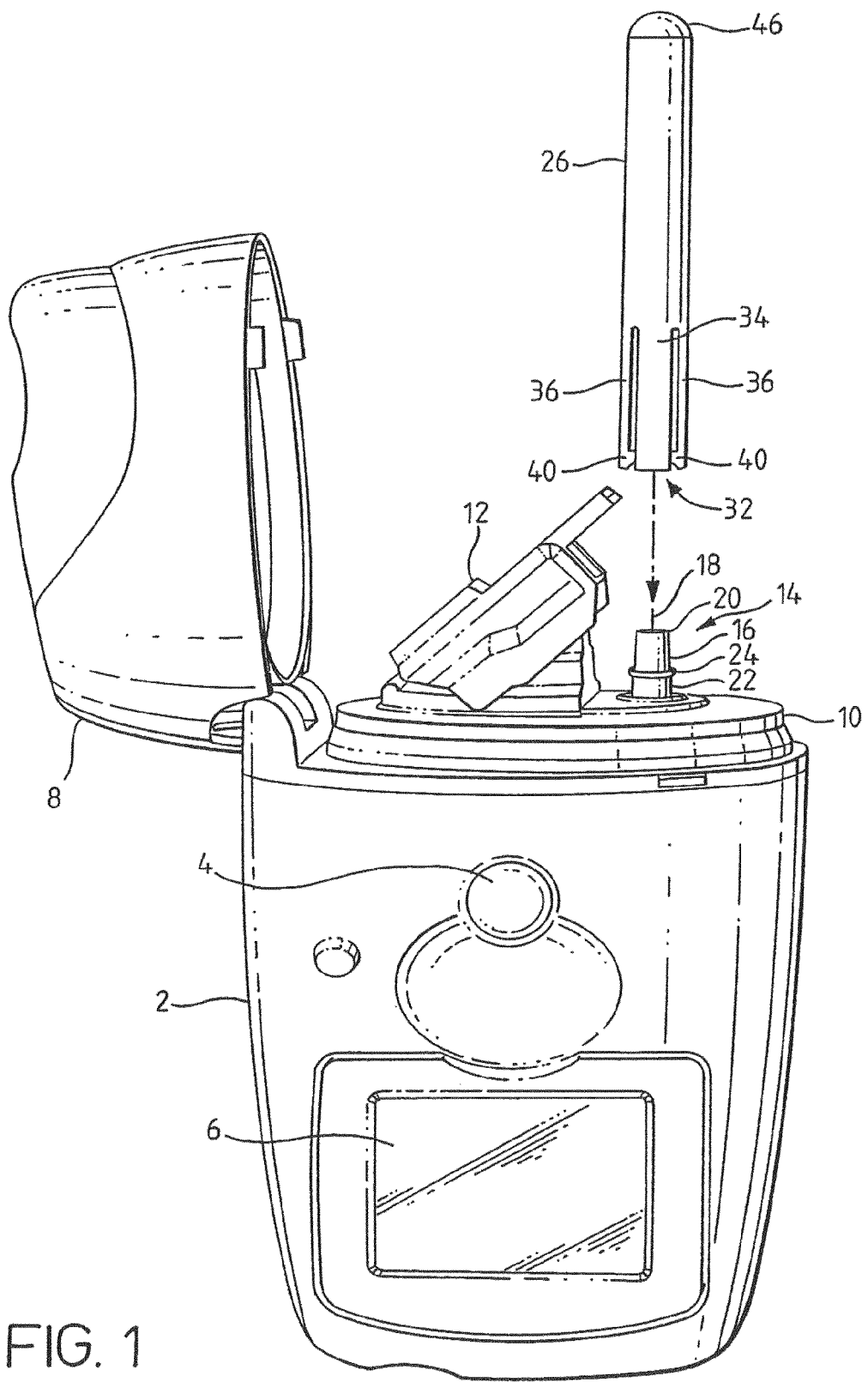
FIG. 1 shows blood sampling equipment including a lancet removal tool.

The blood sampling equipment shown in FIG. 1 is constructed and operated generally along the lines disclosed in EP 1112717A, and is adapted to determine the amount of glucose in the blood of a patient.

The equipment comprises a body 2 which accommodates analysis means for processing a sample of blood taken from a patient. On its outside, the body 2 has control elements such as a pushbutton 4 and a screen 6 for displaying results.

A cap 8 is hinged to the body 2. A pedestal 10 projects from the body 2 and supports a glucose detector assembly 12 and a lancet 14.

The lancet 14 is carried by a lancet device provided in the body 2. The lancet device is powered, for example by a spring arrangement or a pneumatic system, so as to perform an operative stroke to puncture the skin of a patient.

For operation, a one-shot glucose sensing element is fitted to the glucose detector assembly 12, the lancet 14 is fitted to the lancet device, and the cap 8 is closed over the pedestal 10. The cap 8 has a small aperture which, when the cap 8 is closed, is disposed opposite the tip of the lancet 14.

The end of the cap 8 is placed against the skin of a patient, for example on the patient's forearm, and the equipment is activated. A vacuum pump within the body 2 creates a vacuum within the cap 8, the vacuum being supported at the hole in the cap 8 by sealing contact between the cap and the patient's skin. When the required vacuum has been achieved, the lancet device is automatically operated and the lancet 14 momentarily projects through the hole in the cap 8 to pierce the patient's skin. This generates a flow of blood which is taken up by the glucose sensing element on the assembly 12 to be analysed by the processing means in the body 2, so as eventually to display a reading representing glucose level on the screen 6.

The lancet itself comprises a body 16 carrying a sharply pointed needle 18. The body 16 comprises two cylindrical portions 20, 22 with a projections in the form of a circumferential rib 24 between them. The lancing needle 18 is mounted on the end of the cylindrical portion 20, while the cylindrical portion 22 is received by the lancet device within the body 2. The cylindrical portion 22 has a larger diameter than the cylindrical portion 20.

The cylindrical portion 22 is a friction fit in a cup forming part of the lancing device within the body 2. Examples of lancing devices are disclosed in EP 1112717A.

Upon completion of a blood sampling operation, the lancet 14 is contaminated with blood, and must be disposed of safely. This is achieved by use of a lancet removal tool 26. As shown in FIG. 1, the tool is positioned above the lancet 14.

The tool 26 is shown in greater detail in FIGS. 4 to 8, and comprises an elongate cylindrical body 28. The body 28 is hollow and its internal cavity 30 is open to the exterior at an expandable opening 32. The opening 32 is bounded by two oppositely disposed wall portions 34 of the body and by two oppositely disposed resilient elements in the form of fingers 36. The fingers 36 are integral with the body and are separated from the wall by longitudinally extending slots 38. As shown in FIG. 6, the thickness of the fingers 36 increases in the direction towards the opening 32. The fingers 36 are provided with inwardly directed projections 40 in the form of barbs which have an oblique face 42 directed outwardly of the opening 32, and a shoulder 44 directed inwardly of the hollow interior 30 of the body 28.

At the end of the body 28 away from the opening 32, a cap 46 is provided. The cap is releasably fitted to the body 28, and has a cylindrical centre bore 48 of smaller diameter than that of the hollow interior 30.

Referring again to FIG. 1, it will be appreciated that downward movement of the lancet removal tool 26 from the position shown in FIG. 1 will bring the lower end of the tool (as shown) into contact with the lancet 14. The projections 40 on the fingers 36 will ride over the upper cylindrical portion 16, and subsequently over the rib 24, owing to the ramp action of the oblique faces 42. This action spreads the fingers 36 apart, so expanding the opening 32 to accommodate the body 16 of the lancet 14.

Figure 2:
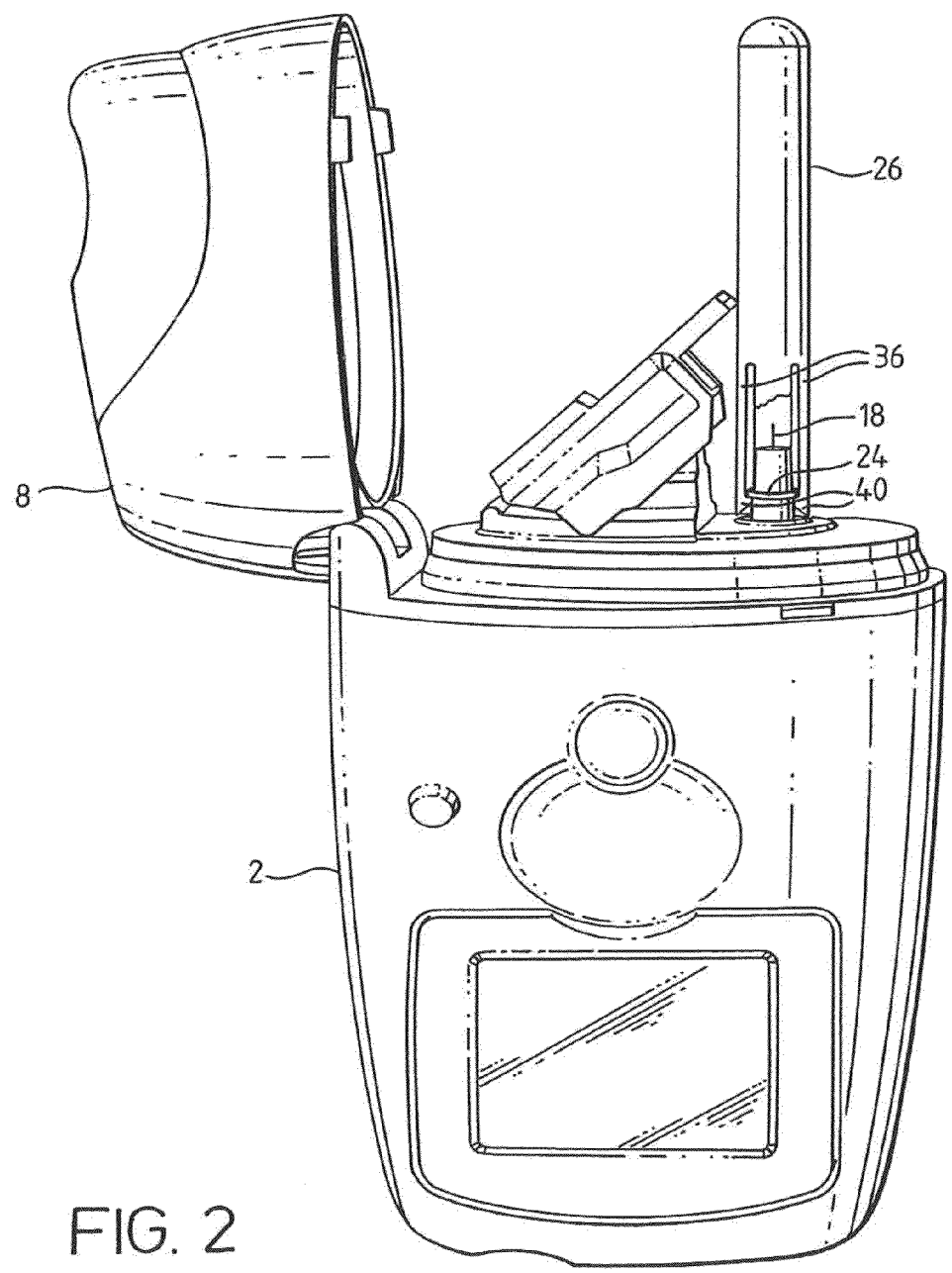
FIG. 2 shows the blood sampling equipment of FIG. 1 with the tool engaging a lancet.

Once the projections 40 have passed the rib 24, the fingers 36 will snap inwards again with the shoulders 44 facing the rib 24, as shown in FIG. 2. In this condition, the pointed needle 18 is safely contained within the opening 32, surrounded by the fingers 36 and the wall portions 34.

Figure 3:
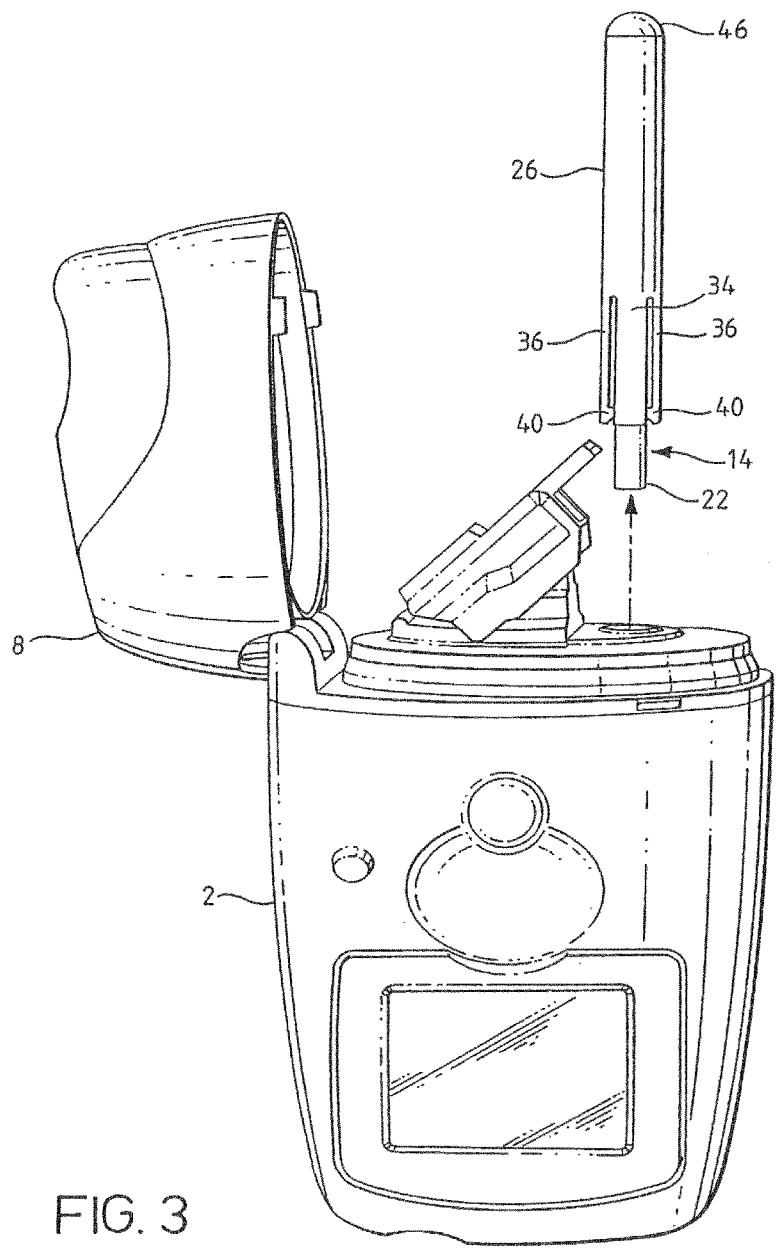
FIG. 3 shows the blood sampling equipment with the lancet removed from the equipment by the tool.

Subsequently, the user simply pulls the tool 26 upwardly by hand, as shown in FIG. 3, to withdraw the lancet as a whole from the lancet device within the body 2. The grip on the rib 24, and possibly frictional engagement between the ends of the projections 40 and the lower cylindrical portion 22 is adequate to overcome the frictional engagement between the cylindrical portion 22 and the lancet device. Once the lancet 14 is clear of the body 2, the tool can be inverted to allow the lancet 14 to fall into the interior 30 of the body 28, possibly assisted by finger pressure on the end of the cylindrical portion 22.

The first lancet to be received in tool 26 can fall to the end of the body 28 closed by the cap 46. The pointed needle 18 can then be accommodated in the recess 48. As a result, movement of the lancet 14 is arrested by abutment of the body 16 of the lancet with the transverse surface of the cap 46, so avoiding contact between the lancet needle 18 and any part of the interior of the tool. The lancet 14 can then be stored within the tool 26 until it is convenient to dispose of it. Subsequent lancets 14 can be removed from the blood sampling equipment and accumulated within the tool 26, in which case the accumulated lancets will lie end-to-end within the interior 30.

At an appropriate time, the individual lancets 14 can be discharged from the tool 26 into a disposal bin by removing the cap 46 and tipping the lancets out to fall under gravity. Alternatively, the tool 26, together with the or each accumulated lancet within it, can be disposed of.

It will be appreciated that, once the tool 26 has been placed over the lancet 14 as shown in FIG. 2, the needle 18 is shielded from contact by the user, so avoiding any possibility of needlestick injury or cross-infection with infected blood. The device thus provides a safe means for the removal and subsequent disposal of used lancets.

Although the present invention has been described with reference to a lancet used in blood sampling apparatus as shown in FIGS. 1 to 3, it will appreciated that the use of the tool is not confined to such applications. For example, the tool may be used with simple lancet devices without provision for blood analysis. Also, although the lancet 14 is described as having a rib 24 which is engaged by the projections 40, the lancet may have other formations, including recesses, for this purposes.

A removable cap may be provided to enclose the open end of the tool 26 when not in use. The cap may, for example, have a clip for enabling the tool to be retained in a user's pocket in the manner of a pen.

The invention claimed is:

1. A system comprising:
    a lancet device;
    at least one lancet for use with the lancet device and removable therefrom; and
    a tool for removing the at least one lancet from the lancet device, the tool comprising a hollow body having an expandable opening at a distal end thereof defined by at least one resilient wall portion, wherein the opening is outwardly expandable from an unexpanded condition to an expanded condition under the resilient action of the at least one resilient wall portion, wherein a transverse dimension of the opening is smaller than a transverse dimension of the lancet when in the unexpanded condition and encases the transverse dimension of the lancet when in the expanded condition, and wherein the tool comprises a removable cap at a proximal end of the hollow body.

2. A system as claimed in claim 1, further comprising a plurality of lancets, the tool hollow body having an internal length sufficient for accommodating therein the plurality of lancets arranged end-to-end.

3. A system as claimed in claim 1, wherein the at least one resilient wall portion comprises an inwardly directed projection engageable with the transverse dimension of the lancet to expand the opening.

4. A system as claimed in claim 3, wherein the transverse dimension of the at least one lancet is provided by a circumferential rib extending about the lancet.

5. A system as claimed in claim 4, wherein the inwardly directed projection comprises a distally facing ramped surface configured for slidably engaging with the rib.

6. A system as claimed in claim 5, wherein the inwardly directed projection further comprises a shoulder positioned proximally of the ramped surface and configured for engaging with the circumferential rib wherein the engaged lancet is irremovable from the opening.

7. A system as claimed in claim 1, further comprising a housing body which accommodates the lancet device, means for sampling body fluid, and means for analyzing the sampled body fluid.

8. A system as claimed in claim 7, further comprising user control elements provided within the housing body.

9. A system as claimed in claim 7, wherein the body fluid is blood and the means for analyzing comprises means for determining the concentration of an analyte within the blood.

10. A system as claimed in claim 9, wherein the analyte is glucose.

* * * * *